United States Patent [19]

Buerstinghaus et al.

[11] 4,267,121
[45] May 12, 1981

[54] PREPARATION OF 2,2-DIMETHYL-4-CYANO-BUTYRALDOXIME N-METHYL-CARBAMATE

[75] Inventors: Rainer Buerstinghaus, Weinheim-Luetzelsachsen; Karl-Heinz Koenig, Frankenthal; Karl Kiehs, Lampertheim, all of Fed. Rep. of Germany

[73] Assignee: BASF Aktiengesellschaft, Fed. Rep. of Germany

[21] Appl. No.: 73,993

[22] Filed: Sep. 10, 1979

[30] Foreign Application Priority Data

Sep. 25, 1978 [DE] Fed. Rep. of Germany ....... 2841714

[51] Int. Cl.$^3$ ................. C07C 120/00; C07C 121/16
[52] U.S. Cl. ................. 260/465.4; 424/304; 564/255
[58] Field of Search ....................... 260/465.4, 566 AC

[56] References Cited

U.S. PATENT DOCUMENTS

| | | | |
|---|---|---|---|
| 3,621,049 | 11/1971 | Addor et al. | 260/465.4 |
| 3,681,505 | 8/1972 | Addor et al. | 424/327 |
| 3,882,176 | 5/1975 | Deye | 260/566 AC X |
| 3,932,509 | 1/1976 | Gatzi | 260/566 AC |
| 3,980,693 | 9/1976 | Kuhle et al. | 260/566 AC X |
| 3,991,092 | 11/1976 | Henderson, Jr. et al. | 260/429.9 |
| 4,052,194 | 10/1977 | Wilcox | 260/566 AC X |
| 4,079,147 | 3/1978 | Brandes et al. | 260/566 AC X |
| 4,117,154 | 9/1978 | Stetter et al. | 260/566 AC X |

*Primary Examiner*—Joseph Paul Brust
*Attorney, Agent, or Firm*—Keil & Witherspoon

[57] ABSTRACT

A process for the preparation of 2,2-dimethyl-4-cyano-butyraldoxime N-methyl-carbamate wherein 2,2-dimethyl-4-cyano-butyraldoxime is reacted with an at least equimolar amount of methylcarbamic acid chloride in the form of a concentrated solution of at least 8 moles thereof per liter of inert organic solvent, in the presence of from 1.05 to 2 moles of a tertiary aliphatic amine per mole of 2,2-dimethyl-4-cyano-butyraldoxime, at from 0° to 30° C.

1 Claim, No Drawings

PREPARATION OF 2,2-DIMETHYL-4-CYANO-BUTYRALDOXIME N-METHYL-CARBAMATE

The present invention relates to a process for the preparation of 2,2-dimethyl-4-cyano-butyraldoxime N-methylcarbamate, which product may be used as an insecticide and acaricide (U.S. Pat. Nos. 3,621,049 and 3,681,505).

The preparation of 2,2-dimethyl-4-cyano-butyraldoxime N-methylcarbamate by reacting 2,2-dimethyl-4-cyano-butyraldoxime with methyl isocyanate in the presence of an inert solvent and of a catalytic amount of an organic amine is disclosed in U.S. Pat. No. 3,681,505. The handling and storage of methyl isocyanate, however, is technically rather troublesome, due to the chemical, physical and toxicological properties of this material (cf. Ullmanns Encyclopädie der technischen Chemie, 4th edition, volume 13, pages 347–357 (1977)).

We have found that 2,2-dimethyl-4-cyano-butyraldoxime N-methylcarbamate is obtained in good yield and high purity if 2,2-dimethyl-4-cyano-butyraldoxime is reacted with an at least equimolar amount of methylcarbamic acid chloride in the form of a concentrated solution of at least 8 moles thereof per liter of inert organic solvent, in the presence of from 1.05 to 2 moles of a tertiary aliphatic amine per mole of 2,2-dimethyl-4-cyano-butyraldoxime, at from 0° to 30° C.

The reaction can be represented by the following equation:

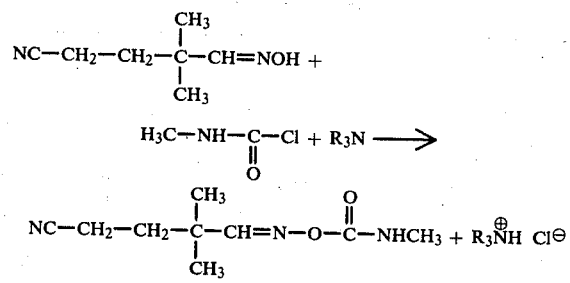

Using the process according to the invention, the reaction, surprisingly, takes only 10–15 minutes. If on the other hand the aldoxime is reacted with a dilute solution of methylcarbamic acid chloride in an inert organic solvent in the presence of not less than an equimolar amount of tertiary aliphatic amine, the reaction takes place substantially more slowly. The reaction time is 20 hours or more and the yield is less than in the process according to the invention, since the low heat stability of 2,2-dimethyl-4-cyano-butyraldoxime N-methylcarbamate leads to undesirable decomposition products (U.S. Pat. No. 3,991,092).

Furthermore, when using the process according to the invention, the additional step of the conventional industrial preparation of methyl isocyanate from methylcarbamic acid chloride is not needed, since the latter material can be employed directly.

Using the process according to the invention, methylcarbamic acid chloride is employed in not less than the equimolar amount based on 2,2-dimethyl-4-cyano-butyraldoxime, and is in fact advantageously used in from 10-fold to 20-fold excess. The methylcarbamic acid chloride is employed in the form of a concentrated solution containing at least 8 moles of this compound per liter of inert organic solvent.

Suitable solvents for preparing such concentrated solutions of methylcarbamic acid chloride include chloroform, methylene chloride, carbon tetrachloride, 1,2-dichloroethane, diethyl ether, dioxan, tetrahydrofuran, acetone, methyl ethyl ketone, benzene and toluene.

To bind the hydrogen chloride formed, the reaction is carried out in the presence of a tertiary aliphatic amine, which is employed in excess, advantageously in a molar ratio of from 1.05 to 2. Examples of suitable amines are trialkylamines, eg. triethylamine, dimethylethylamine and dimethylisopropylamine, or dialkylcycloalkylamines, eg. dimethylcyclohexylamine, or tertiary heterocyclic amines, eg. 1-methyl-pyrrolidine and 1-methylpiperidine.

The reaction is allowed to take place at from 0° to 30° C., preferably from 20° to 25° C.

Advantageously, the reaction is carried out by adding a concentrated solution of methylcarbamic acid chloride in an inert organic solvent dropwise to the 2,2-dimethyl-4-cyano-butyraldoxime dissolved in an excess of amine. The reaction temperature is kept at from 0° to 30° C. by external cooling. The reaction is complete after 10–15 minutes. The volatile constituents of the reaction mixture are then stripped off under reduced pressure and the product is extracted from the residue by means of a suitable solvent, for example methylene chloride. After having stripped off the solvent, the carbamate remains in the form of a pale yellow oil, which crystallizes completely after seeding.

The Examples which follow illustrate how the process according to the invention may be carried out, in comparison to the reaction with a dilute methylcarbamic acid chloride solution, which is either added directly to the 2,2-dimethyl-4-cyano-butyraldoxime and the amine, or is formed by intially introducing solvent into the reaction mixture.

EXAMPLE 1

(a) Reaction with a concentrated methylcarbamic acid chloride solution 105.1 parts by weight of 2,2-dimethyl-4-cyanobutyraldoxime are dissolved in 113.7 parts by weight of triethylamine. A solution of 77 parts by weight of methylcarbamic acid chloride in 100 parts by volume of chloroform are added dropwise, whilst stirring and keeping the mixture at from 20° to 25° C. by external cooling. 15 minutes after completion of the addition, the volatile constituents of the reaction mixture are stripped off at 0.13 mbar and 25° C., and the residue is extracted with 200 parts by volume of methylene chloride. The extract is washed once with dilute sodium bicarbonate solution and three times with water, and is dried over sodium sulfate. After evaporating off the solvent, 122.6 parts by weight, corresponding to a yield of 83% of theory, of a pale yellow syrupy oil remain. After stripping off the last proportions of solvent under reduced pressure, this oil crystallizes throughout; melting point 41°–43° C. According to $^1$H-NMR spectroscopy, the product obtained is pure 2,2-dimethyl-4-cyano-butyraldoxime N-methylcarbamate.

(b) Reaction with a dilute methylcarbamic acid chloride solution 105.1 parts by weight of 2,2-dimethyl-4-cyanobutyraldoxime and 113.7 parts by weight of triethylamine are dissolved in 300 parts by volume of chloroform. A solution of 77 parts by weight of methylcarbamic acid chloride in 100 parts by volume of chloroform is then added dropwise whilst stirring and cooling so as to keep the mixture at from 20° to 25° C. Stirring is then continued for 20 hours at this temperature, after which the precipitate formed is filtered off and the filtrate is concentrated under reduced pressure at 20° C. The oil which remains is taken up in 250 parts by volume of methylene chloride and the solution is washed once with dilute sodium bicarbonate solution and twice with water. After drying the organic phase over sodium sulfate, the solvent is removed under reduced pressure, leaving 118.2 parts by weight of a syrupy oil which according to the $^1$H-NMR spectrum contains at most 86% of 2,2-dimethyl-4-cyano-butyraldoxime N-methylcarbamate. The product cannot be made to crystallize by seeding.

EXAMPLE 2

(a) Reaction with a concentrated methylcarbamic acid chloride solution

A solution of 56.1 parts by weight of methylcarbamic acid chloride in 73 parts by volume of acetone is added, with vigorous stirring, to a solution of 84.1 parts by weight of 2,2-dimethyl-4-cyano-butyraldoxime in 121.4 parts by weight of triethylamine, whilst keeping the mixture at from 20° to 25° C. by external cooling. 15 minutes after completion of the addition, the volatile constituents of the reaction batch are stripped off at 1.1 mbar and 25° C., the residue is extracted with 190 parts by volume of methylene chloride and the organic phase thus obtained is washed three times with water. After it has been dried over sodium sulfate, the solvent is completely removed under reduced pressure, leaving 103 parts by weight (yield: 87% of theory) of a viscous oil which after seeding crystallizes throughout; melting point 40.5°–43° C. According to its $^1$H—NMR spectrum, the product obtained consists of pure 2,2-dimethyl-4-cyano-butryaldoxime N-methylcarbamate.

(b) Reaction with a dilute methylcarbamic acid chloride solution 56.1 parts by weight of 2,2-dimethyl-4-cyano-butyraldoxime and 44.5 parts by weight of triethylamine are dissolved in 300 parts by volume of acetone. A solution of 37.4 parts by weight of methylcarbamic acid chloride in 100 parts by volume of acetone is then added dropwise, whilst stirring and cooling, the rate of addition being such that the reaction mixture throughout remains at from 20° to 25° C. Stirring is then continued for 20 hours at this temperature, after which the precipitate formed is filtered off and the filtrate is concentrated under reduced pressure at 20° C. The oil which remains is taken up in 250 parts by volume of methylene chloride and the solution is washed once with dilute sodium bicarbonate solution and twice with water. After drying the organic phase over sodium sulfate, the solvent is removed under reduced pressure, leaving 65.7 parts by weight of a viscous pale yellow oil which according to its $^1$H—NMR spectrum contains at most 88% of 2,2-dimethyl-4-cyano-butyraldoxime N-methylcarbamate.

EXAMPLE 3

A reaction mixture of 2,2-dimethyl-4-cyano-butyraldoxime, triethylamine, methylcarbamic acid chloride and acetone, as described in Example 2(b), is stirred for 48 hours at 20°–25° C. During the reaction, samples are taken for examination by $^1$H—NMR spectroscopy; the following relation between reaction time and conversion is found:

| time (h) | 0.083 | 0.25 | 1 | 2 | 5 | 18 | 24 | 48 |
| --- | --- | --- | --- | --- | --- | --- | --- | --- |
| mole % of 2,2-dimethyl-4-cyano-butyraldoxime N-methylcarbamate | 23 | 36 | 48 | 64 | 77 | 91 | 90 | 89 |

We claim:

1. A process for the preparation of 2,2-dimethyl-4-cyano-butyraldoxime N-methyl-carbamate which comprises: contacting 2,2-dimethyl-4-cyano-butyraldoxime with an at least equimolar amount of methylcarbamic acid chloride in the form of a concentrated solution of at least 8 moles thereof per liter of inert organic solvent, in the presence of from 1.05 to 2 moles of a tertiary aliphatic amine per mole of 2,2-dimethyl-4-cyano-butyraldoxime, at from 0° to 30° C., whereby the reaction is completed within 15 minutes after the reactants have been added.

* * * * *